United States Patent
Chen et al.

(10) Patent No.: US 10,882,888 B2
(45) Date of Patent: Jan. 5, 2021

(54) METHOD FOR EXTRACTING 2',3'-CYCLIC NUCLEOSIDE MONOPHOSPHATES

(71) Applicant: SHANDONG UNIVERSITY, Jinan (CN)

(72) Inventors: Xiulan Chen, Jinan (CN); Yuzhong Zhang, Jinan (CN); Ang Liu, Jinan (CN); Yang Yu, Jinan (CN); Binbin Xie, Jinan (CN); Qilong Qin, Jinan (CN); Xiaoyan Song, Jinan (CN); Mei Shi, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 427 days.

(21) Appl. No.: 15/765,043

(22) PCT Filed: Oct. 24, 2016

(86) PCT No.: PCT/CN2016/103058
§ 371 (c)(1),
(2) Date: Mar. 30, 2018

(87) PCT Pub. No.: WO2017/148163
PCT Pub. Date: Sep. 8, 2017

(65) Prior Publication Data
US 2019/0048044 A1    Feb. 14, 2019

(30) Foreign Application Priority Data
Feb. 29, 2016 (CN) .......................... 2016 1 0112458

(51) Int. Cl.
| | |
|---|---|
| *C07K 14/245* | (2006.01) |
| *C12P 19/32* | (2006.01) |
| *C12P 19/30* | (2006.01) |
| *C12N 1/06* | (2006.01) |
| *C12Q 1/6876* | (2018.01) |
| *C12N 1/20* | (2006.01) |
| *C12N 15/70* | (2006.01) |
| *C12Q 1/6806* | (2018.01) |
| *C12Q 1/686* | (2018.01) |

(52) U.S. Cl.
CPC ............ *C07K 14/245* (2013.01); *C12N 1/066* (2013.01); *C12N 1/20* (2013.01); *C12N 15/70* (2013.01); *C12P 19/305* (2013.01); *C12P 19/32* (2013.01); *C12Q 1/686* (2013.01); *C12Q 1/6806* (2013.01); *C12Q 1/6876* (2013.01)

(58) Field of Classification Search
None
See application file for complete search history.

(56) References Cited

U.S. PATENT DOCUMENTS

| | | | |
|---|---|---|---|
| 10,351,857 B2 * | 7/2019 | Chen ..................... | C12P 19/305 |
| 2019/0048353 A1 * | 2/2019 | Chen ..................... | C07K 14/195 |

OTHER PUBLICATIONS

Sequence Alignment of SEQ ID No. 1 with AY072083. Search conducted on Jun. 12, 2020, 2 pages. (Year: 2020).*
Sequence Alignment of SEQ ID No. 1 with AV816635. Search conducted on Jun. 12, 2020, 2 pages. (Year: 2020).*
Sequence Alignment of SEQ ID No. 2 with AAF09550. Search conducted on Jun. 12, 2020, 2 pages. (Year: 2020).*
Sequence Alignment of SEQ ID No. 2 with EH543926. Search conducted on Jun. 12, 2020, 2 pages. (Year: 2020).*
Sequence Alignment of SEQ ID No. 2 with LA861796. Search conducted on Jun. 12, 2020, 2 pages. (Year: 2020).*

* cited by examiner

*Primary Examiner* — Channing S Mahatan
(74) *Attorney, Agent, or Firm* — CBM Patent Consulting, LLC

(57) ABSTRACT

It relates to a method for preparation of four kinds of 2', 3'-cNMPs (2', 3'-cAMP, 2', 3'-cGMP, 2', 3'-cCMP and 2', 3'-cUMP), comprising steps of: (1) extract genomic DNA and amplify gene If3; (2) ligate If3 gene to expression plasmid to construct a recombinant vector, and transfer the recombinant vector to *E. coli* to obtain a recombinant strain. Cultivate the recombinant strain and collect the fermentation broth; (3) collect the cells form the fermentation broth and disrupt the cells, and then purify the recombinant protein IF3 from the cell extract by $Ni^{2+}$-nitrilotriacetic acid resin. Incubate the recombinant protein IF3 solution at 0° C. for 3 days to release 2', 3'-cNMPs from IF3, and centrifuge the solution; (4) Ultrafiltrate the supernatant to remove proteins, and prepare four kinds of 2', 3'-cNMPs by high-performance liquid chromatographic (HPLC) on a $C_{18}$ reversed-phase column.

Figure 1:
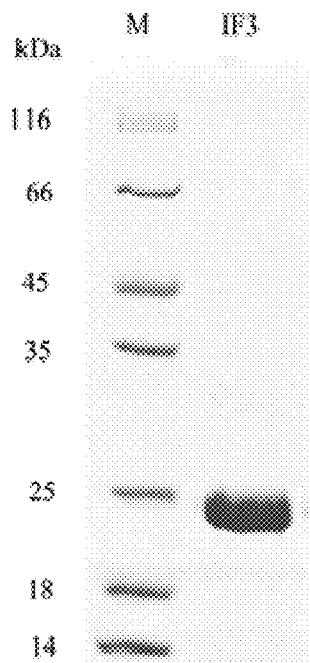

8 Claims, 4 Drawing Sheets
Specification includes a Sequence Listing.

METHOD FOR EXTRACTING 2',3'-CYCLIC NUCLEOSIDE MONOPHOSPHATES

TECHNICAL FIELD

The present invention relates to a method for preparation of four kinds of 2', 3'-cNMPs (2', 3'-cAMP, 2', 3'-cGMP, 2', 3'-cCMP and 2', 3'-cUMP) simultaneously by a recombinant protein expressed in *Escherichia coli*. It belongs to biotechnological field.

BACKGROUND

Cyclic nucleotides are important second messengers in living cells, involving in a range of intracellular physiological pathways. Earl. W. Sutheland first proposed that 3', 5'-cAMP is a second messenger in human body in 1965. Thereafter, 3', 5'-cGMP, 3', 5'-cCMP, 3', 5'-cUMP, c-di-GMP, c-di-AMP and cGAMP were successively found in various biological cells to involve in the regulation of many intracellular signaling pathways as second messengers. Except 3', 5'-cNMPs, 2', 3'-cNMPs are also found in mammals, plants and bacteria. Compared to 3', 5'-cNMPs, studies on the physiological roles of 2', 3'-cNMPs are still limited. It was found that 2', 3'-cNMPs may be involved in tissue and cells damage. In damaged tissue or cells, 2', 3'-cNMPs increase significantly. It was also found that 2', 3'-cAMP can induce apoptosis by activate the mitochondrial permeability transition pores. In addition, the phosphorylation level of 2', 3'-cyclic nucleotide-3' phosphodiesterase increased in brain cells during HIV infection. These findings on 2', 3'-cNMPs are arousing more and more interests of researchers.

As 2', 3'-cNMPs attract more and more attention, there will be an increasing demand of 2', 3'-cNMPs in scientific research and pharmaceutical application. Now, all available 2', 3'-cNMPs are chemically synthesized. However, chemical synthesis have disadvantages such as low yield and high price, which limit the application of 2', 3'-cNMPs to some extent.

SUMMARY OF THE INVENTION

To overcome the limitation of current technology, here a method is provided to prepare four kinds of 2', 3'-cNMPs simultaneously by biotechnology. In this method, four kinds of 2', 3'-cNMPs can be denovo synthesized by the growth of recombinant *Escherichia coli*, without the need of a specific precursor, and can be prepared rapidly by purifying the recombinant protein IF3 from recombinant *E. coli*.

DETAILED DESCRIPTION

In this invention, preparation of 2', 3'-cNMPs includes the following steps:

(1) Extract genomic DNA from *E. coli* K12, and amplify the If3 gene by PCR. The primers sequences used in PCR are as follows: F-GGAATTCCATATGAT-TAAAGGCGGAAAACG (SEQ ID NO: 1), R-CCGCTCGAGCTGTTTCTTCTTAGG (SEQ ID NO: 2);

(2) Digest the If3 gene obtained from step (1) with specific restriction enzymes. Clone the digested If3 gene into pET-22b (+) vector digested with the same enzymes to generate the expression vector. Then transfer the expression vector into *E. coli* BL21 (DE3) to obtain a recombinant strain. Culture the recombination strain by fermentation.

(3) Collect the cells from the fermentation broth from step (2) by centrifugation, break the cells and purify the recombinant protein IF3 from the cell extract by $Ni^{2+}$-nitrilotriacetic acid resin. Incubate the purified IF3 solution at 0° C. for 2.5-3.5 days to release 2', 3'-cNMPs from IF3. Collect the supernatant containing 2', 3'-cNMPs.

(4) Ultrafiltrate the supernatant from step (3) to remove proteins, and subject the filtrate to high-performance liquid chromatographic (HPLC) on a $C_{18}$ reversed-phase column to separate the four kinds of 2', 3'-cNMPs. Collect the four kinds of 2', 3'-cNMPs separately.

The preferred PCR amplification system (50 μL) in step (1) of the present invention is as follows:

| | |
|---|---|
| Sterilized distilled water | 32.2 μl |
| 5× TransStart FastPfu buffer | 10 μl |
| dNTP mix | 5 μl |
| Primer F (50 μM) | 0.4 μl |
| Primer R (50 μM) | 0.4 μl |
| Genomic DNA | 1 μl |
| TransStart FastPfu DNA polymerase | 1 μl |

PCR reaction conditions in step 1 are as follows:

Pre-denature at 95° C. for 5 min; denature at 95° C. for 30 sec; anneal at 55° C. for 30 sec; extend at 72° C. for 30 sec; 30 cycles; finally extend at 72° C. for 5 min.

The specific restriction enzymes used for DNA digestion in step (2) are Nde I and Xho I.

The preferred digestion reaction system in step (2) is as follows:

| | |
|---|---|
| Buffer | 2 μl |
| plasmid pET-22b/gene If3 | 8 μl |
| Restriction enzyme Nde I | 1 μl |
| Restriction enzyme Xho I | 1 μl |
| Sterilized distilled water | 8 μl |

Reaction condition: Incubation at 37° C. for 30 min.
ligation reaction system in step (2) is as follows:

| | |
|---|---|
| Digested plasmid pET-22b | 1 μl |
| Digested gene If3 | 4 μl |
| Solution I | 5 μl |

Reaction condition: Incubation at 16° C. overnight

The preferred procedure for strain cultivation in step (2) is as below:

Cultivate the recombinant strain at 35-38° C. and 150-200 rpm until the $OD_{600}$ reaches 0.8; then incubate the culture at 18-22° C. and 100-140 rpm for 30 min; add 0.1 mM isopropul-β-D-thiogalactopyranoside to the culture as an inducer and continue the cultivation at 18-22° C. and 100-140 rpm for 22-25 hours.

The preferred culture medium in step (2) is Luria-Bertani (LB) medium (one liter medium contains 10 g NaCl, 10 g peptone and 5 g yeast extract dissolved in distilled water, pH 8.0).

The preferred cell disruption procedure in step (3) is as follows:

Cells are collected from the fermentation broth and suspended in lysis buffer (50 mM Tris-HCl, 150 mM NaCl, pH 8.0). Then the cells are broken under pressure of 950~1050 bar. After centrifugation at 12,000 rpm for 50 min, the supernatant containing the recombinant protein is collected.

The preferred purification procedure for recombinant protein IF3 by $Ni^{2+}$-nitrilotriacetic acid resin in step (3) is as follows:

Load the supernatant from step (3) on a nickel column. After the supernatant flowed through the nickel column, equilibrate the column with 20 ml lysis buffer. Wash the column with 20 ml washing buffer (50 mM Tris-HCl, 150 mM NaCl, 20 mM imidazole, pH 8.0). Elute the column with 10 ml elution buffer (50 mM Tris-HCl, 150 mM NaCl, 250 mM imidazole, pH 8.0). Collect the eluent containing recombinant protein IF3.

The preferred molecular weight cutoff for ultrafiltration in step (4) is 3000 Da.

The preferred protocol for sample separation in step (4) is as follows (the values are times in minutes and percentage of buffer B used): 0.0, 0; 2.5, 0; 5.0, 30; 10.0, 60; 14.0, 100; 21.0, 100; 22.0, 50 and 23.0, 0 at a flow rate of 10 ml/min. The detection wavelength is 254 nm.

The preferred mobile phases in step (4) used in the gradient program are as follows: buffer A (10 mM ammonium acetate, pH 5.0) and buffer B (75% (v/v) buffer A, 25% (v/v) methanol).

Beneficial Effects

1. The present invention offers a method for the preparation of four kinds of 2', 3'-cNMPs simultaneously from recombinant *E. coli*. Four kinds of 2', 3'-cNMPs can be denovo synthesized by bacterial fermentation without the need of a specific precursor. This method is simple, convenient and has less contamination compared to chemical synthesis. Five milligram 2', 3'-cNMPs can be obtained from 1 L fermentation broth.

2. In the present invention, *E. coli* fermentation is used to produce 2', 3'-cNMPs. *E. coli* has a known genetic background and a fast growing speed, which is beneficial for further increasing the yield of 2', 3'-cNMPs via bioengineering.

FIGURE LEGENDS

FIG. 1. SDS-PAGE analysis of the recombinant protein IF3 purified by $Ni^{2+}$-nitrilotriacetic acid resin. M, protein marker; IF3, recombinant protein IF3.

Figure 2:
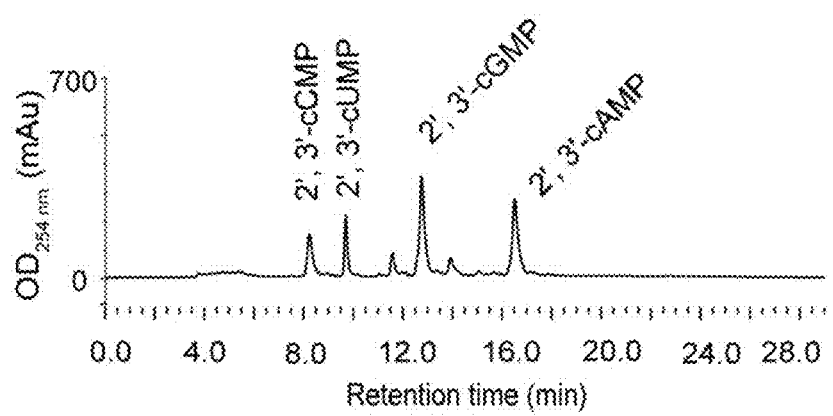

FIG. 2. Separation of four kinds of 2', 3'-cNMPs by HPLC.

Figure 3:
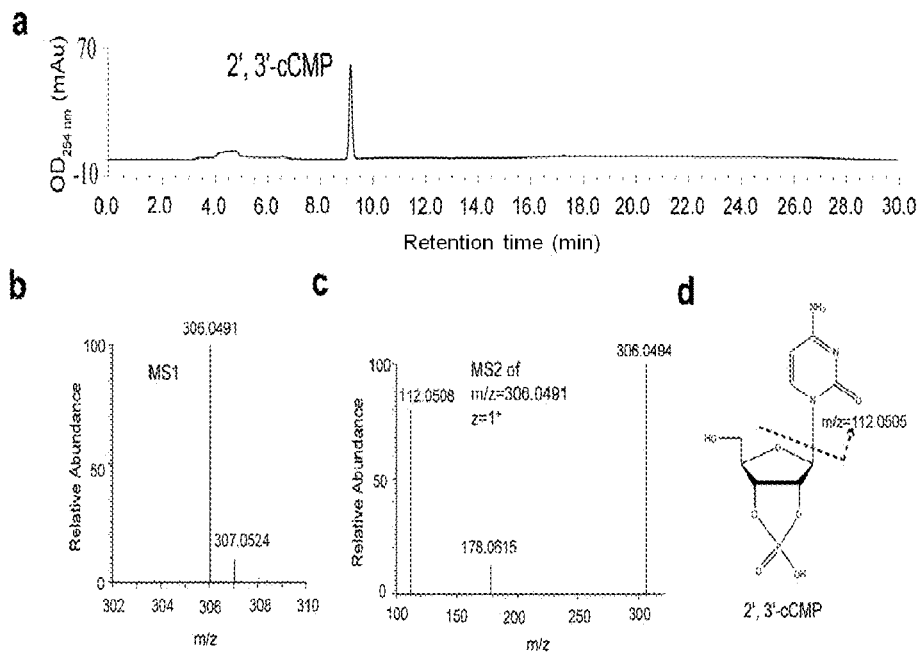

FIG. 3. HPLC and LC-MS/MS analyses of purified 2', 3'-cCMP includes: HPLC analysis of purified 2', 3'-cCMP (a); LC-MS analysis of purified 2', 3'-cCMP, LC-MS chromatogram revealed the m/z ratio of S1 is 306.0491 (z=1), corresponding to the ion extraction of cCMP (b); Tandem mass ($MS^2$) spectra (c) after higher-energy collision dissociation (HCD) fragmentation of the ion with m/z=306.0491 (z=1) from the $MS^1$ scan shown in (b). Fragmentation pathways of cCMP are shown in (d); Structure of 2', 3'-cCMP (d).

Figure 4:
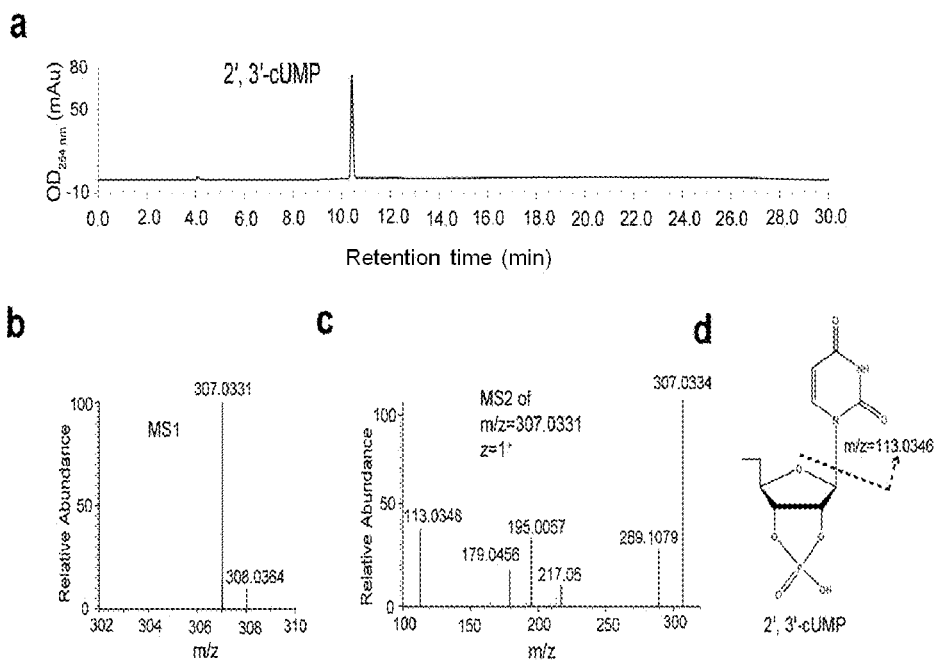

FIG. 4. HPLC and LC-MS/MS analysis of purified 2', 3'-cUMP includes: HPLC analysis of purified 2', 3'-cUMP (a); LC-MS analysis of purified 2', 3'-cUMP, the m/z ratio of purified 2', 3'-cUMP is 307.0331 (z=1), corresponding to the ion extraction of cUMP (b); Tandem mass ($MS^2$) spectra (c) after higher-energy collision dissociation fragmentation of the ion with m/z=307.0331 (z=1) from the $MS^1$ scan shown in (b). Fragmentation pathways of cCMP are shown in (d); The structure of 2', 3'-cUMP (d).

Figure 5:
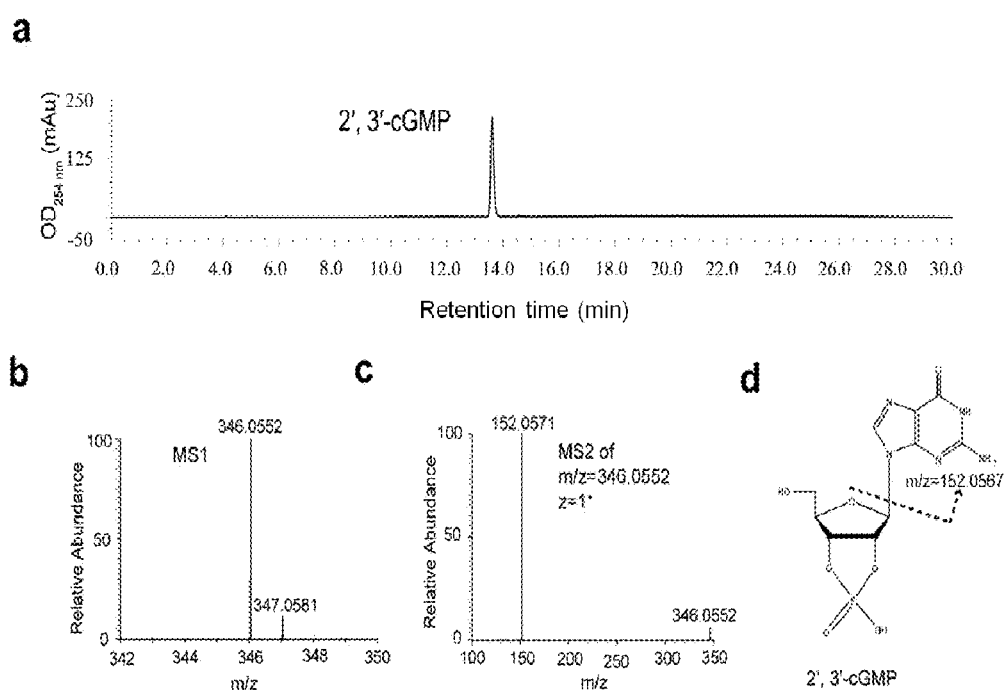

FIG. 5. HPLC and LC-MS/MS analysis of purified 2', 3'-cGMP includes: HPLC analysis of purified 2', 3'-cGMP (a); LC-MS analysis of purified 2', 3'-cGMP, The m/z ratio of purified 2', 3'-cGMP is 346.0552 (z=1), corresponding to the ion extraction of cGMP (b); Tandem mass ($MS^2$) spectra (c) after higher-energy collision dissociation fragmentation of the ion with m/z=346.0552 (z=1) from the $MS^1$ scan shown in (b). Fragmentation pathways of cCMP are shown in (d); The structure of 2', 3'-cGMP (d).

Figure 6:
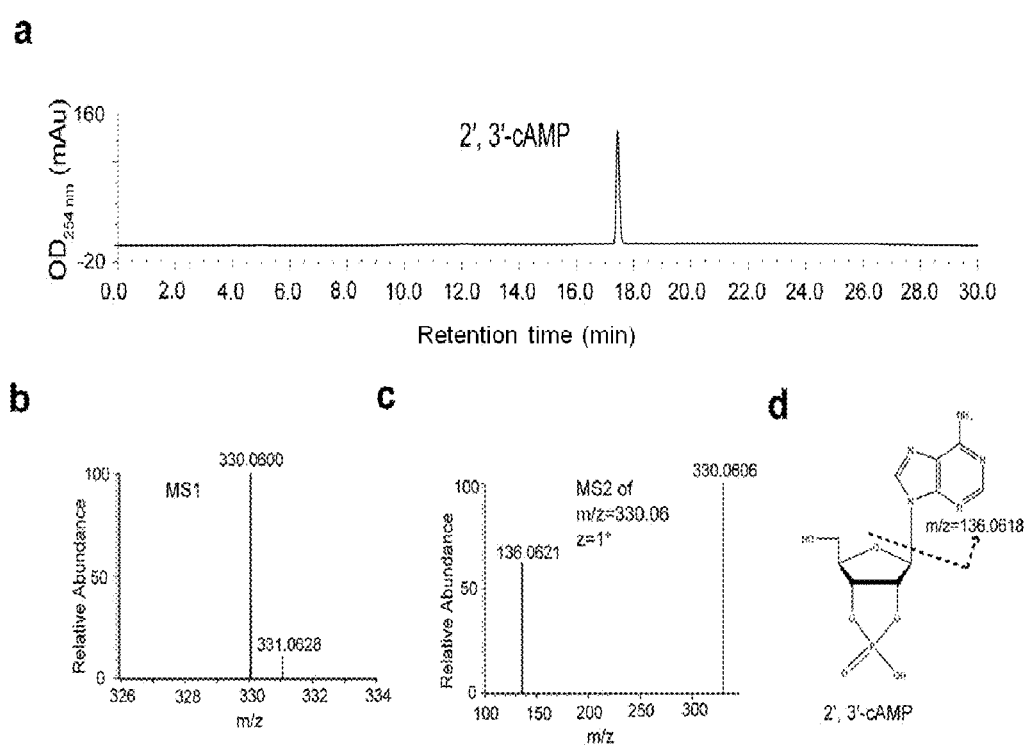

FIG. 6. HPLC and LC-MS/MS analysis of purified 2', 3'-cAMP includes: HPLC analysis of purified 2', 3'-cAMP (a); LC-MS analysis of purified 2', 3'-cAMP, the m/z ratio of purified 2', 3'-cAMP is 330.06 (z=1), corresponding to the ion extraction of cAMP (b); Tandem mass ($MS^2$) spectra (c) after higher-energy collision dissociation fragmentation of the ion with m/z=330.06 (z=1) from the $MS^1$ scan shown in (b). Fragmentation pathways of cCMP are shown in (d); The structure of 2', 3'-cAMP (d).

ILLUSTRATIVE EMBODIMENTS

The following comprises a list of illustrative embodiments according to the present invention which represent various embodiments of the present invention. These examples are offered to illustrate, but not to limit the present invention. *E. coli* K12 was purchased from China Center of Industrial Culture Collection (CICC) in these examples. The address is: the 6th building, 24th courtyard of the Jiuxianqiao middle road, Chaoyang district, Beijing, China. The accession number is CICC 10424.

*E. coli* BL21 (DE3) competent cell in these examples was purchased from Beijing TransGen Biotech Co., Ltd. The address is: the 4th floor of the B-3 building, Dongsheng Science Park of Zhongguancun, 66th of Xixiaokou Road, Haidian District, Beijing, China.

Example 1

The method to construct the recombinant strain includes the following steps:

1. Cloning Gene If3 from *E. coli* K12.

1.1 Extraction of Genomic DNA from *E. coli* K12

The genomic DNA was extracted according to the instructions of genome extraction kit from Bioteke Corporation, China.

1.2 Design and Synthesis of the Primers

Primers were designed according to the If3 gene sequence. The primer sequences were as follows:

```
F:
                                              (SEQ ID NO: 1)
GGAATTCCATATGATTAAAGGCGGAAAACG;

R:
                                              (SEQ ID NO: 2)
CCGCTCGAGCTGTTTCTTCTTAGG.
```

Primers were synthesized by Sangon Biotech (Shanghai) Co., Ltd, China.

1.3 Amplification of Gene If3 by PCR and its Recovery (1) Gene If3 was amplified with primers F and R, using the genomic DNA as a template. Conditions for PCR reaction were as follows: pre-denaturing at 95° C. for 5 min; denaturing at 95° C. for 30 sec; annealing at 55° C. for 30 sec; extending at 72° C. for 30 sec; 30 cycles; finally extending at 72° C. for 5 min.

The PCR amplification system (50 µl) was as follows:

| | |
|---|---|
| Sterilized distilled water | 32.2 µl |
| 5× TransStart FastPfu buffer | 10 µl |
| dNTP mix | 5 µl |
| Primer F (50 µM) | 0.4 µl |
| Primer R (50 µM) | 0.4 µl |
| Genomic DNA | 1 µl |
| TransStart FastPfu DNA polymerase | 1 µl |

(2) The PCR products were separated by 1% agarose gel electrophoresis. The DNA fragment of gene If3 was recovered from the gel with DNA purification kit from Omega.

2. Construction of the Recombinant Expression Vector and Recombinant Expression Strain.

(1) Digestion of the Gene and Expression Vector

The If3 gene obtained from step 1 and vector pET-22b were digested with restriction enzymes Nde I and Xho I. The reaction system for digestion was as follows:

| | |
|---|---|
| Buffer | 2 µl |
| Expression plasmid pET-22b/gene If3 | 8 µl |
| Restriction enzyme NdeI | 1 µl |
| Restriction enzyme XhoI | 1 µl |
| Sterilized distilled water | 8 µl |

The sample was mixed smoothly, centrifuged for 2 sec and then incubated at 37° C. for 30 min. The digested products were separated by 1% agarose gel electrophoresis, and the target DNA segments of gene If3 and vector pET-22b were recovered from the gel using DNA purification kit from Omega.

(2) Ligation of Gene If3 and Vector pET-22b to Construct the Recombinant pET-22b-If3 Vector The reaction system was as follows:

| | |
|---|---|
| Digested vector pET-22b | 1 µl |
| Digested gene If3 | 4 µl |
| Solution I | 5 µl |

The sample was mixed smoothly, centrifuged for 2 sec and incubated at 16° C. overnight. Then the recombinant pET-22b-If3 vector was constructed.

(4) The recombinant pET-22b-If3 vector was transformed into E. coli BL21 (DE3) according to the method described in Molecular Cloning Manual, and transformed E. coli cells were obtained.

(5) The transformed E. coli cells were spread on LB agar plate containing 100 µg/ml ampicilin and cultivated at 37° C. overnight.

(6) The recombinant strain was screened from the plate and verified by recombinant plasmid extraction and sequencing in Sangon Biotech (Shanghai) Co., Ltd.

Example 2

1. Fermentation of the Recombinant Strain (1) Cultivation of Inoculum

The recombinant E. coli strain was inoculated in liquid LB medium containing 100 µg/ml ampicillin and incubated at 180 rpm and 37° C. overnight to obtain inoculum.

(2) The inoculum was inoculated in 1 L fermentation medium with 1% inoculum size and cultivated at 180 rpm and 35-38° C. until the $OD_{600}$ reached 0.8. Then, 0.1 mM isopropul-β-D-thiogalactopyranoside (IPTG) was added in the culture, which was further cultivated at 120 rpm and 20° C. for 24 hours.

2. Purification of Recombinant Protein IF3

(1) Buffers used for Purification

Lysis buffer: 50 mM Tris-HCl, 150 mM NaCl, pH 8.0

Washing buffer: 50 mM Tris-HCl, 150 mM NaCl, 20 mM imidazole, pH 8.0

Elution buffer: 50 mM Tris-HCl, 150 mM NaCl, 250 mM imidazole, pH 8.0

(2) The cells of the fermented recombinant E. coli strain from step (1) were collected by centrifugation at 10,000 rpm, resuspended in 50 ml lysis buffer (for 1 liter broth), and broken at the pressure of 1,000 bar.

(3) The solution from step (2) was centrifuged at 12,000 rpm and 4° C. for 50 min.

(4) The supernatant from step (3) was loaded on a nickel column containing 2 ml nickel gel. After the supernatant flowed through the nickel column, equilibrate the column with 20 ml lysis buffer. Wash the column with washing buffer 20 ml, and elute the recombinant protein IF3 from the column with 10 ml elution buffer. Collect the eluent, which was the recombinant protein IF3 solution.

Example 3

1. Extraction of 2', 3'-cNMPs (1) The recombinant protein IF3 solution obtained in example 2 was incubated at 0° C. for 3 days to release 2', 3'-cNMPs from IF3, then centrifuged at 12,000 rpm for 20 min, and the supernatant was collected.

(2) The supernatant obtained from step (1) was ultrafiltrated by using an ultrafiltration tube with a molecular weight cut-off of 3,000 Da to remove proteins. The filtrate containing four kinds of 2', 3'-cNMPs was collected.

2. Purification of Four Kinds of 2', 3'-cNMPs (2', 3'-cAMP, 2', 3'-cGMP, 2', 3'-cCMP and 2', 3'-cUMP).

(1) Four kinds of 2', 3'-cNMPs in the filtrate were separated by high-performance liquid chromatographic (HPLC) on a $C_{18}$ reversed-phase column and collected separately.

The mobile phases used in the gradient program were as follows: buffer A (10 mM ammonium acetate, pH 5.0) and buffer B (75% (v/v) buffer A, 25% (v/v) methanol).

(2) The protocol used for purification was as follows (the values are times in minutes and percentage of buffer B used): 0.0, 0; 2.5, 0; 5.0, 30; 10.0, 60; 14.0, 100; 21.0, 100; 22.0, 50 and 23.0, 0 at a flow rate of 10 ml/min. The detection wavelength was 254 nm.

The result of HPLC separation of four kinds of 2', 3'-cNMPs was shown in FIG. 2. HPLC and LC-MS/MS analyses of each kind of purified 2', 3'-cNMPs were shown in FIGS. 3 to 6.

What is claimed is:

1. A method for preparing 2', 3'-cNMPs comprising steps of:
  (1) extracting genomic DNA from *Escherichia coli* K12, and amplifying translation initiation factor If3 gene which encodes translation initiation factor IF3 protein by polymerase chain reaction (PCR), wherein the F-GGAATTCCATATGATTAAAGGCGGAAAACG (SEQ ID NO: 1) and R-CCGCTCGAGCTGTTTCTTCTTAGG (SEQ ID NO: 2);
  (2) digesting the gene If3 from step (1) with specific restriction enzymes, ligating the digested If3 gene into vector pET-22b (+) that has been digested with the same restriction enzymes to generate an expression vector, transforming the generated expression vector into *E. coli* BL21 (DE3) to obtain a recombinant strain; c culturing the obtained recombinant strain and collecting the fermentation broth; wherein the restriction enzymes are Nde I and Xho I, and digesting is performed with:

| buffer | 2 μl |
| expression plasmid pET-22b/gene If3 | 8 μl |
| restriction enzyme Nde I | 1 μl |
| restriction enzyme Xho I | 1 μl |
| sterilized distilled water | 8 μl | and under the following condition: water bath at 37° C. for 30 min;
  (3) collecting the cells from the fermentation broth of step (2) by centrifugation, breaking the collected cells and purifying the recombinant protein IF3 therein by $Ni^{2+}$-nitrilotriacetic acid resin to obtain recombinant protein IF3 solution, incubating the recombinant protein IF3 solution at 0° C. for 2.5-3.5 days to release 2', 3'-cNMPs from the recombinant protein IF3, centrifuging the recombinant protein IF3 solution and collecting the supernatant containing 2', 3'-cNMPs;
  (4) ultra-filtrating the supernatant from step (3) to remove proteins and obtain filtrate, and preparing four kinds of 2', 3'-cNMPs from the filtrate by high-performance liquid chromatographic (HPLC) on a $C_{18}$ reversed-phase column.

2. The method of claim 1 wherein the PCR in step (1) is performed with:

| sterilized distilled water | 32.2 μl |
| 5× reaction buffer | 10 μl |
| dNTP mix | 5 μl |
| primer F (50 μM) | 0.4 μl |
| primer R (50 μM) | 0.4 μl |
| genomic DNA | 1 μl |
| DNA polymerase | 1 μl | and under the following conditions:
  pre-denature at 95° C. for 5 min; denature at 95° C. for 30 sec; anneal at 55° C. for 30 sec; extend at 72° C. for 30 sec; 30 cycles; finally extend at 72° C. for 5 min.

3. The method of claim 1 wherein the ligating in step (2) is performed with:

| digested vector pET-22b | 1 μl |
| digested gene If3 | 4 μl |
| solution I | 5 μl | and under the following condition: incubation at 16° C. overnight.

4. The method of claim 1 wherein culturing the recombinant strain in step (2) comprises steps of:
  culturing the recombinant strain at 150-200 rpm and 35-38° C. until the $OD_{600}$ of the culture reaches 0.8; then incubating the culture at 100-140 rpm and 18-22° C. for 30 min;
  adding 0.1 mM isopropul-β-D-thiogalactopyranoside into the culture as an inducer and continue to cultivate continuing to culture the strain at 100-140 rpm and 18-22° C. for 22-25 hours;

wherein culturing is performed in a Luria-Bertani (LB) medium (1 liter medium contains 10 g NaCl, 10 g peptone and 5 g yeast extract dissolved in distilled water, pH 8.0).

5. The method of claim 1 wherein purifying the recombinant protein IF3 by $Ni^{2+}$-nitrilotriacetic acid resin in step (3) comprises the steps of:

loading the supernatant of step (3) on a nickel column containing 2 ml gel; equilibrating the column with 20 ml lysis buffer after the supernatant passes through the nickel column; washing the column with 20 ml washing buffer, eluting the column with 10 ml elution buffer and collecting the eluent containing the recombinant protein IF3;

wherein the components of the lysis buffer are: 50 mM Tris-HCl, 150 mM NaCl, pH 8.0;

wherein the components of the washing buffer are: 50 mM Tris-HCl, 150 mM NaCl, 20 mM imidazole, pH 8.0;

wherein the components of the elution buffer are: 50 mM Tris-HCl, 150 mM NaCl, 250 mM imidazole, pH 8.0.

6. The method of claim 1 wherein the molecular weight cutoff for ultrafiltration in step (4) is 3000 Da.

7. The method of claim 1 wherein ultra-filtrating in step (4) is as follows (values are times in minutes and percentage of buffer B used): 0.0, 0; 2.5, 0; 5.0, 30; 10.0, 60; 14.0, 100; 21.0, 100; 22.0, 50 and 23.0, 0 at a flow rate of 10 ml/min; the detection wavelength is 254 nm;

mobile phases of the $C_{18}$ reversed-phase column in step (4) are: buffer A (10 mM ammonium acetate, pH 5.0) and buffer B (75% (v/v) buffer A, 25% (v/v) methanol).

8. The method of claim 1 wherein in step (3) the collected cells are suspended in lysis buffer comprising 50 mM Tris-HCl and 150 mM NaCl at pH 8.0, breaking of the collected cells is performed at a pressure of 950-1050 bar, and the centrifugation of the recombinant protein IF3 solution is performed at 12,000 rpm for 50 min.

* * * * *

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: It is synthesized.

<400> SEQUENCE: 1
ggaattccat atgattaaag gcggaaaacg                30

<210> SEQ ID NO 2
<211> LENGTH: 24
<212> TYPE: DNA
<213> ORGANISM: Artificial Sequence
<220> FEATURE:
<223> OTHER INFORMATION: It is synthesized

<400> SEQUENCE: 2
ccgctcgagc tgtttcttct tagg                24